United States Patent [19]

Lebeck et al.

[11] 4,245,638

[45] Jan. 20, 1981

[54] SURGICAL ANASTOMOSIS CLAMPING APPARATUS

[75] Inventors: Harold E. Lebeck, 520 Pine Ave., No. 55, Goleta, Calif. 93017; Donald B. Rhodes, Santa Barbara, Calif.

[73] Assignee: Harold E. Lebeck, Goleta, Calif.

[21] Appl. No.: 958,815

[22] Filed: Nov. 8, 1978

[51] Int. Cl.[3] .............................................. A61B 17/11
[52] U.S. Cl. ................. 128/334 C; 128/346; 128/92 EA
[58] Field of Search ............... 128/334 R, 334 C, 325, 128/346, 92 EA

[56] References Cited

U.S. PATENT DOCUMENTS

| | | | |
|---|---|---|---|
| 1,151,300 | 8/1915 | Soresi | 128/334 C |
| 1,217,637 | 2/1917 | Rink | 128/92 EA |
| 1,308,799 | 7/1919 | Masland | 128/92 EA |
| 3,048,177 | 8/1962 | Takaro | 128/334 C |
| 3,561,448 | 2/1971 | Peternel | 128/334 C |
| 4,165,747 | 8/1979 | Bermant | 128/334 C |

FOREIGN PATENT DOCUMENTS

| | | | |
|---|---|---|---|
| 618821 | 4/1961 | Canada | 128/346 |
| 395074 | 1/1974 | U.S.S.R. | 128/334 C |

*Primary Examiner*—Dalton L. Truluck
*Attorney, Agent, or Firm*—Fulwider, Patton, Rieber, Lee & Utecht

[57] ABSTRACT

Apparatus for particular use in approximating the respective ends of two vas segments that are to be sutured together in a vasectomy reversal, the apparatus including two special clamp assemblies, each for gripping a separate vas segment, and a rotatable lead screw, to which the clamps are coupled, for controllably moving the clamps together. Each clamp includes two concave jaws that are movable toward each other to form a substantially cylindrical seat for conformably receiving and gripping the corresponding vas segment with a controllable pressure, whereby the segments are held in precise axial alignment, without any significant deformation. The two clamps are coupled to the lead screw via separate lead nuts disposed on oppositely threaded portions of the screw, whereby controlled rotation of the lead screw causes the clamps, and thus the vas segments being gripped, to be controllably approximated.

10 Claims, 8 Drawing Figures

U.S. Patent
Jan. 20, 1981
4,245,638
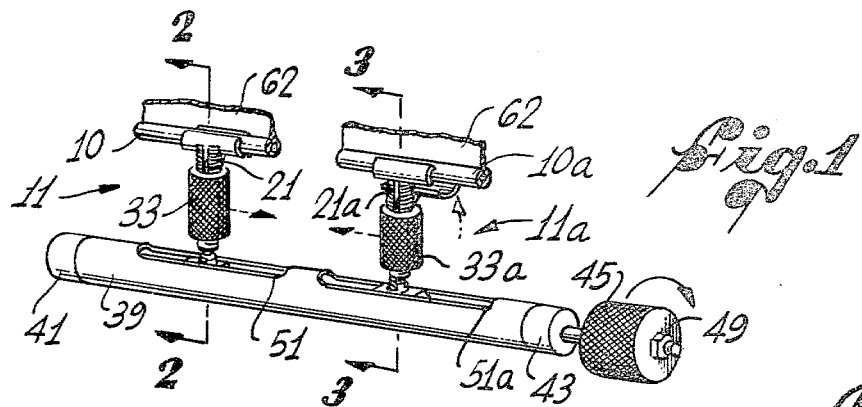
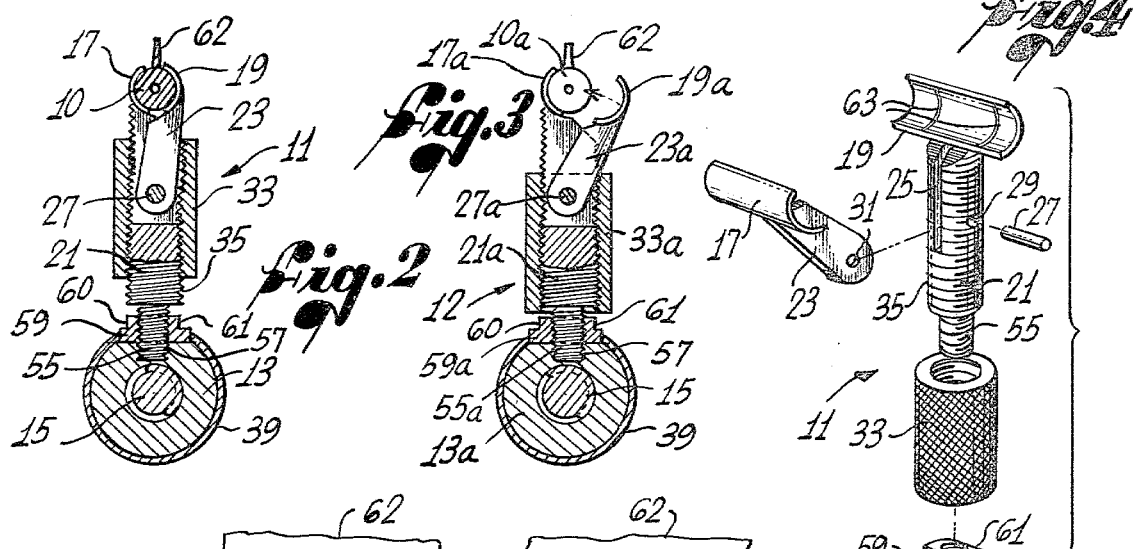
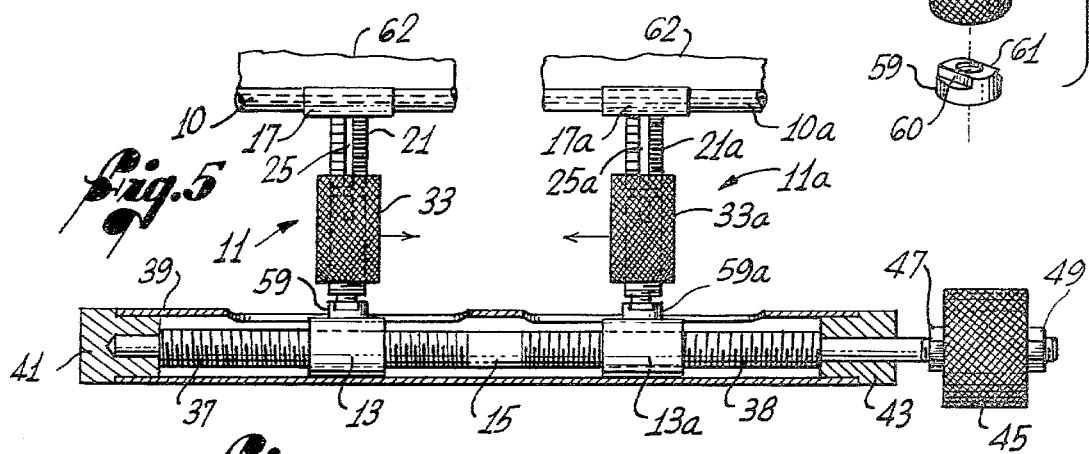
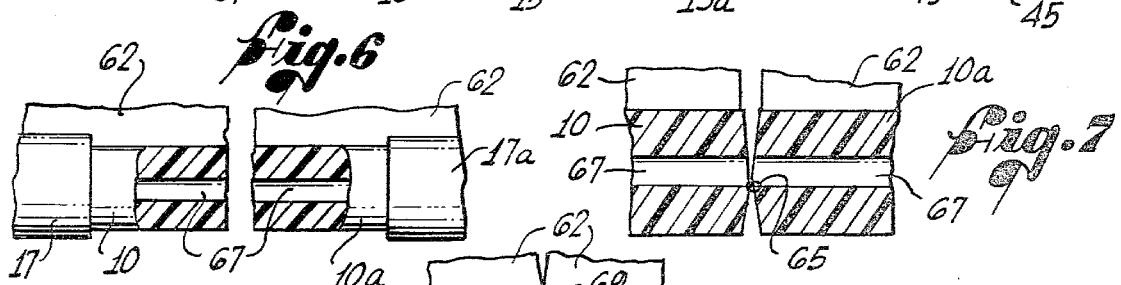
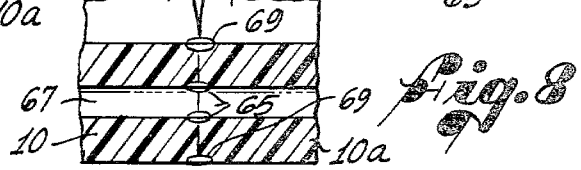

SURGICAL ANASTOMOSIS CLAMPING APPARATUS

BACKGROUND OF THE INVENTION

This invention relates generally to surgical instruments and, more particularly, to surgical clamps for use in the suturing of elongated vessels.

Surgical instruments of this particular type are useful in the approximation of elongated tubular vessels, especially the vas deferens, the fallopian tubes and blood vessels, during surgical anastomosis, and, additionally, in the surgical suturing of fibers, such as nerves and nerve bundles. An instrument of this type typically includes two clamps, each for gripping a separate one of the vessels to be sutured, along with support means for controllably moving the two clamps towards each other, to "approximate" the respective ends of the vessels.

A popular technique for the anastomosis of the vas deferens, i.e., vasectomy reversal or vasovasostomy, was developed by Sherman J. Silber, M.D. and is described in an article written by Silber entitled "Microsurgery in Clinical Urology", appearing in Urology, Vol. VI, No. 2, pp. 150–53, August, 1975. After suitable initial preparation of the two vas segments to be joined together, each of the segments is gripped securely by a separate one of the two clamps of the approximation instrument and the clamps are controllably moved together to approximate the end of the two segments. A plurality of mucosal stitches around the vas lumens are then made, followed by a plurality of adventitia stitches around the periphery of the vas, to secure the two segments together. Since the size of the vas lumens is exceedingly small relative to the size of the vas deferens, itself, it is critical that the approximation instrument maintain the two vas segments in a precise axial alignment during the operation.

Prior approximation instruments, however, have not proven entirely satisfactory for use in vasovasostomy surgery of type described above. One typical approximation instrument of the prior art includes two clamps in the form of spring-loaded clips, each for gripping a separate one of the two vas segments to be joined together. A first clamp is coupled to a stable base member and a second clamp is coupled to a rotatable lead screw, whereby rotation of the screw causes the second clamp to be moved toward the first, to approximate the two vas segments. The instrument has not proven entirely satisfactory, however, primarily because the spring-clip clamps offer little resistance to the movement of the vas segments out of axial alignment with respect to each other. Additionally, the spring clips ordinarily cause a significant deformation of the segments, and, since only one of the two clips is movable relative to the base of the instrument, an undesirable stress on the corresponding vas segment can result when the segments are being approximated. As a result of these drawbacks, excessive time is ordinarily required to complete the surgical suturing of the segments.

Other known approximation instruments for use in vasovasostomy surgery utilize clamps that have resilient linings and that are held together by friction. These instruments, likewise, have not been found effective in maintaining a precise alignment of the vas segments to be joined. As a result, excessive time is required to complete a surgical vasovasostomy.

Other approximation instruments, for particular use in the anastomosis of blood vessels, are disclosed in Canadian Pat. No. 618,821, issued to C.A Reindorf and entitled "Surgical Clamp", and in U.S. Pat. No. 3,561,448, issued to K. Peternel and entitled "Blood Vessel Suturing Apparatus". Both prior patents disclose approximation apparatus having a pair of clamps mounted on the ends of arms that are pivotally connected to each other. The apparatus disclosed by Reindorf includes clamps in the form of spring-loaded clips, similar to the spring-loaded clips of the vasovasostomy instrument described above, and thus it is susceptible to many of the same drawbacks. The instrument disclosed in the Peternel patent includes clamps that have cylindrical seats for conformably receiving the vessels to be sutured together and holding them in place by means of air suction. Although the vessels are inhibited from moving relative to the clamps, the pivotal arrangement of the clamps allows the vessels to be positioned in axial alignment with each other only when they are in actual abutment. Moreover, the pressure with which each clamp grips the corresponding vessel is not controllable, and the clamps are not readily adaptable for use with vessels of varying sizes. Additionally, the bulkiness of the instrument can sometimes interfere with the suturing of the vessels.

It will be appreciated from the foregoing that there is a definite need for a surgical instrument for use in the approximation of elongated vessels and fibers during surgical anastomosis, wherein the vessels are gripped with a controllable pressure, without being significantly deformed, and wherein the vessels are maintained in a precise axial alignment throughout the approximation procedure, thereby facilitating a rapid suturing of the vessels. The present invention fulfill this need

SUMMARY OF THE INVENTION

Basically, the present invention is embodied in an improved surgical approximation apparatus for use in the anastomosis of elongated vessels and fibers. The apparatus includes two clamps, each for gripping a separate one of the two vessels to be joined together, along with support means for controllably moving the two clamps toward each other and thereby approximating the respective ends of the vessels.

In accordance with the invention, each of the clamps includes two concave jaws, which, together, form a seat to receive and hold a separate one of the enlongated vessels in precise axial alignment with respect to the other. Further, the size of the seat formed by the two jaws can be varied, whereby a variety of vessel sizes can be accommodated, and whereby the vessels are gripped with a controllable pressure. The clamp operates to distribute the gripping force, whereby no substantial deformation of the vessels is caused.

More particularly, a surgical approximation apparatus constructed in accordance with the present invention is especially adaptable for use in vasovasostomy surgery, wherein the severed segments of the vas deferens are sutured together. The support means of the approximation apparatus includes an elongated lead screw having one end threaded in a first direction, and the other end threaded in the opposite direction. One of the clamps is coupled via a stanchion to a lead nut threadedly engaging one end of the lead screw, and the other clamp is coupled via another stanchion to a lead nut threadedly engaging the other end of the screw. The lead screw is journaled within a housing, and the clamp stanchions project through and abut slots formed in the housing, thereby preventing rotation of each nut and its corresponding clamp, about the axis of the lead screw. As a result, rotation of the lead screw causes the respective clamps to be moved toward each other, to approximate the respective ends of the vessels being gripped.

The two jaws included in each clamp are pivotal with respect to each other and are preferably semi-cylindrical in shape, to form a substantially cylindrical seat for receiving the vessel. One of the jaws is mounted at the remote end of the stanchion, and the other is mounted at the remote end of a pivot arm connected at its base to the stanchion. In accordance with one aspect of the invention, the stanchion is externally threaded and adapted to receive an internally threaded collar, which, when rotated with respect to the stanchion, urges the pivot arm to pivot toward the stanchion, and thereby bring the jaws together to grip an elongated vessel properly position therebetween. The pivot arm is received in an elongated slot formed in the stanchion.

In accordance with another aspect of the present invention, the two jaws on each clamp are inhibited from being closed fully, to form a closed cylindrical seat whereby injury to the mesentery of the vas deferens is prevented. This is accomplished by sizing the jaws such that a narrow gap remains between their top sides when they are urged together by the collar.

In accordance with still another aspect of the invention, each clamp includes means for preventing the corresponding vessel from sliding in an axial direction, whereby the relative spacing between the respective ends of the two vessels to be joined can be precisely controlled. Such means can include, for example, a special friction pad secured to the concave inner face of at least one of the jaws, or a special embossed portion formed in such face.

Other aspects and advantages of the present invention will become apparent from the following description of the preferred embodiment, taken in conjunction with the accompanying drawings, which disclose, by way of example, the principles of the invention.

BRIEF DESCRIPTION OF THE DRAWINGS

FIG. 1 is a perspective view of a surgical approximation apparatus embodying the present invention, with a pair of elongated tubular vessels shown being gripped by the two clamps of the apparatus;

FIG. 2 is a sectional view of the apparatus, taken substantially along the line 2—2 in FIG. 1;

FIG. 3 is a sectional view of the apparatus, taken substantially along the line 3—3 in FIG. 1;

FIG. 4 is an exploded perspective view of one clamp of the apparatus of FIG. 1;

FIG. 5 is an elevational view of the apparatus of FIG. 1, with the housing being broken away to reveal the lead screw;

FIG. 6 is an enlarged fragmentary sectional view of the two tubular vessels after they have been approximated;

FIG. 7 is a enlarged sectional view of the two vessels, after the first suture has been made; and FIG. 8 is an enlarged sectional view of the two vessels, after suturing has been completed.

DESCRIPTION OF THE PREFERRED EMBODIMENT

Referring now to the exemplary drawings, and particularly to FIGS. 1 and 5, there is shown a surgical approximation apparatus constructed in accordance with the preferred embodiment of the present invention. The apparatus has particular use in vasovasostomy surgery, wherein two segments 10 and 10a of the vas deferens are approximated and sutured together. The apparatus operates to grip the two vas segments securely and to controllably move them together, while maintaining them in precise axial alignment.

The apparatus includes two identical clamp assemblies 11 and 11a each for gripping a separate one of the respective vas segments 10 and 10a. Although only one of the clamp assemblies will be described in detail, it will be understood that both assemblies are preferably identical. The elements of the clamp assembly 11 are identified by numerals, alone, while elements for the other clamp assembly 11a are identified by corresponding numerals, followed by the letter "a". The clamp assemblies 11 and 11a are coupled by means of lead nuts 13 and 13a, respectively, to a lead screw 15, which operates to controllably move the two clamp assemblies towards each other, and thereby approximate the two vas segments being gripped by the assemblies.

In accordance with the invention, the clamp assembly 11 includes two elongated jaws 17 and 19 having facing concave portions that are movable toward each other to grip the corresponding vas segment 10 with a controllable pressure, and wherein the two segments are maintained in precise axial alignment. Each jaw is preferably semi-cylindrical in shape, whereby the two jaws cooperate to form a cylindrical seat to conformably receive the vas segment. As best shown in FIGS. 2 through 4, the jaw 17 is attached to the remote end of a stanchion 21 that is coupled to the corresponding lead nut 13, and the other jaw 19 is attached to the remote end of an arm 23 that is pivotally mounted, at its base, to the stanchion. The pivot arm 23 is received within a longitudinal slot 25 formed in the stanchion 21, and the arm is pivotally coupled to the stanchion by means of a pin 27 that is inserted through bore holes 29 and 31 formed in the stanchion and the arm, respectively.

The jaws 17 and 19 are urged toward each other in a pivotal fashion by means of an internally threaded collar 33 that engages corresponding threads 35 formed on the external surface of the stanchion 21. Rotation of the collar in the proper angular direction will cause it to move upwardly on the stanchion, to controllably urge the pivot arm 23 into the slot 25, and thereby approximate the two jaws. The exterior surface of the collar is knurled, thereby allowing the surgeon to grip and control its rotation more easily.

Rotation of the collar 33 thus controls the size of the seat formed by the jaws 17 and 19, whereby a range of vas segment sizes can be accommodated, and the pressure with which the segment is gripped can be precisely controlled. Since the seat formed by the jaws is substantially cylindrical in shape, and since the vas segment is substantially conformably received within the seat, the segment can ordinarily be gripped with sufficient pressure to inhibit relative slipping, without causing any significant deformation.

In accordance with another aspect of the present invention, the two opposite halves of the lead screw 15 include oppositely threaded sections 37 and 37a, each for threadedly receiving a separate one of the respective lead nuts 13 and 13a. Further, the apparatus includes means for preventing the lead nuts from rotating whenever the lead screw is rotated, whereby a controlled rotation of the lead screw will cause the two lead nuts, and thus the two clamp assemblies 11 and 11a, to be controllably moved together.

The lead screw 15 is disposed within a generally cylindrical housing 39, and it is rotated in bearing 41 and 43 disposed at the ends of the housing. The lead screw has an end portion that extends completely through the bearing 43, and receives a knurled knob 45 that can be used to manually rotate the screw. The knob 45 can be secured to the screw 15 by any suitable means, such as by retaining nuts 47 and 49.

The two stanchions 21 and 21a, which are attached to the respective lead nuts 13 and 13a, project through elongated slots 51 and 51a formed in the housing 39. The stanchion 21 has a threaded base portion 55 for engaging a corresponding threaded bore 57 in the lead nut 13, and it is fixed to the lead nut by means of a lock nut 59. The lock nut is generally cylindrical in shape, with notches 60 and 61 formed in it to enable it to be rotated relative to the stanchion by means of a wrench (not shown). The cylindrical portions of the lock nuts 59 and 59a abut the two sides of the corresponding housing slot 51 or 53, to prevent rotation of the lead nuts, and, therefore, the clamp assemblies 11 and 11a, relative to the housing 39. Thus as the lead screw 15 is turned by means of the knurled knob 45, the two clamp assemblies are controllably moved toward or away from each other. Since both clamps are moved at the same rate, stresses on the two vas segments 10 and 10a are equalized.

The two clamp assemblies 11 and 11a must be initially aligned with respect to each other, so that when the two vas segments 10 and 10a are being gripped, they will be maintained in a proper axial alignment. This initial alignment can be accomplished using a straight cylindrical rod (not shown) having approximately the same diameter as the vas segments to be sutured together. The rod is initially gripped by both clamp assemblies, with the stanchions 21 and 21a loosely coupled to their respective lead nuts 13 and 13a. The lock nuts 59 and 59a are then tightened, to secure the stanchions in position, whereby, after the rod has been removed, the jaws of the respective clamp assemblies will be properly axially aligned.

In accordance with another aspect of the present invention, the two jaws 17 and 19 on each clamp assembly 11 are inhibited from being closed sufficiently to form a closed cylindrical seat, whereby injury to the mesentery 62 of the vas deferens is prevented. This is accomplished by forming at least one of the two jaws in an incomplete semi-cylindrical cycle shape. As a result, when the collar 33 is rotated fully to pivot the pivot arm 23 into the longitudinal slot 25 in the stanchion 21 (see FIG. 2), the lower sides of the jaws will be in close proximity or in abutment with each other (depending on the size of the vessel being gripped), but the upper sides of the jaws will be in spaced relationship with each other, to accommodate the presence of the mesentery.

In accordance with still another aspect of the present invention, the concave surface of each jaw 17 and 19 includes friction means for preventing the corresponding vas segment 10 and 10a from sliding in an axial direction, whereby the relative spacing between the respective ends of the two segments can be precisely controlled. As shown in FIG. 4, the friction means can take the form of a pair of circumferential ferrules of ridges 63 formed on the concave surface of each jaw. Alternatively, such means can include, for example, a special friction pad secured to the concave surface or a roughened texture formed on the surface, itself.

When the apparatus of the present invention is being used in vasovasostomy surgery, each of the two vas segments 10 and 10a to be joined together is gripped by a separate one of the respective clamp assemblies 11 and 11a, with a small portion of each segment projecting beyond the inward edge of the clamp. The lead screw 15 is then rotated by means of the knurled knob 45 to approximate the two vas segments, as shown in FIG. 6, until there is a gap of approximately one-eighth inch between the respective ends of the segments. As shown in FIGS. 7 and 8, approximately four mucosal stitches 65 are then made in a conventional manner around the perimeter of the vas lumens 67, to secure the segments together. This is followed by approximately four adventitia stitches 69 made in the exterior perimeter of the vas segments, to strengthen the coupling between them. Since the two vas segments are held securely by the apparatus, in a precise axial alignment and without any substantial deformation occurring, the suturing can be readily accomplished within a significantly reduced amount of time. It should be appreciated that each vas segment must project beyond the inward edge of its clamp assembly by an amount that permits the segment to be stretched sufficiently to join each other, but that does not permit the segments to flex readily out of axial alignment.

From the foregoing description, it should be apparent that the present invention provides an improved surgical approximation apparatus for use in approximating elongated tubular vessels or fibers during anastomosis surgery. The apparatus includes special clamp assemblies for securely gripping the two vessels, without any significant deformation, and for maintaining them in precise axial alignment. Thus, the apparatus enables a substantial reduction in the time ordinarily required for suturing the vessels together.

Although the invention has been described in detail with reference to its presently preferred embodiment, it will be understood by one of ordinary skill in the art that various modifications can be made without departing from the spirit and scope of the invention. Accordingly, it is not intended that the invention be limited, except as by the appended claims.

We claim:

1. Apparatus for use in approximating the respective ends of two elongated vessels, said apparatus comprising:
    an elongated lead screw having a first portion threaded in a first direction and a second portion threaded in a second direction;
    a first nut threadedly engaging the first portion of said lead screw;
    a second nut threadedly engaging the second portion of said lead screw;
    first and second clamps coupled to said first and second nuts, respectively, each clamp adapted to grip a separate one of the elongated vessels with a controllable pressure, and without causing any significant deformation thereof, said vessels being maintained in axial alignment with respect to each other; and means for preventing rotation of said first and second nuts about the axis of said lead screw, whereby rotation of said lead screw effects an axial movement of said first and second clamps toward each other, to approximate the respective ends of the elongated vessels.

2. Apparatus as defined in claim 1, wherein:

each of said first and second clamps includes an elongated stanchion for coupling the clamp to the corresponding nut; and said preventing means includes a housing disposed around said lead screw and said first and second nuts, and with respect to which the lead screw can be rotated, said housing having an elongated slot formed therein, a portion of each of said stanchions being received within said slot, in slidable abutment with an edge thereof, whereby each of said clamps is prevented from rotating about the axis of said lead screw.

3. Apparatus as defined in claim 1, wherein each of said first and second clamps includes:

a first jaw having a concave gripping surface, a second jaw having a concave gripping surface disposed adjacent the gripping surface of first jaw, and control means for controllably moving said first and secnod jaws toward each other, wherein the respective gripping surfacces of the jaws together form a seat for receiving the corresponding vessel and gripping it with a controllable pressure, without causing any significant deformation thereof;

4. Apparatus as defined in claim 1, wherein:

each of said clamps further includes a stanchion having a base end coupled to the corresponding one of said first and second nuts, and a remote end for carrying said first jaw, the exterior surface of said stanchion having a threaded portion, and a pivot arm having a base end pivotally coupled to said stanchion, and a remote end for carrying said second jaw; and said control means includes a collar having an internally threaded portion for threadedly engaging the threaded portion of the corresponding stanchion, whereby rotation of the collar in a prescribed angular direction causes the collar to move toward the remote end of the stanchion, and thereby urges the pivot arm in a pivotal fashion toward the stanchion.

5. Apparatus as defined in claim 1, wherein the gripping surface of each of said jaws is substantially in the form of an elongated half cylinder whereby the seat formed by said first and second jaws conformably receives an elongated vessel that is substantially circular in cross-section.

6. Apparatus for use in approximating the respective ends of a pair of elongated tubular vessels, substantially circular in cross-section, to facilitate a surgical anastomosis of the vessels, said apparatus comprising:

first and second clamps for controllably gripping the respective vessels, each of said clamps including first and second jaws, each having a concave gripping surface substantially in the form of an elongated half cylinder, a stanchion having a base end and a remote end, said remote end carrying said first jaw, the exterior surface of said stanchion having a threaded portion, a pivot arm having a base end pivotally coupled to said stanchion, and a remote end for carrying said second jaw, said stanchion having an elongated slot formed therein for receiving the pivot arm when the arm is urged to pivot toward the stanchion, and a collar having an internally threaded portion for threadedly engaging the threaded portion of the stanchion, whereby rotation of the collar in a prescribed angular direction causes the collar to move toward the remote end of the stanchion and thereby urge the pivot arm to move in a pivotal fashion toward the stanchion, whereby the respective gripping surfaces of said first and second jaws cooperate to form a substantially cylindrical seat for conformably receiving the correspnding vessel and gripping it with a controllable pressure, without causing any significant deformation thereof;

an elongated lead screw having a first portion threaded in a first direction and a second portion threaded in a second direction;

a first nut threadedly engaging the first portion of said lead screw, said first clamp being coupled to said first nut;

a second nut threadedly engaging the second portion of said lead screw, said second clamp being coupled to said second nut; and means for inhibiting rotation of said first and second nuts about the axis of said lead screw, whereby rotation of said lead screw effects an axial movement of said first and second clamps toward each other, to approximate the respective ends of the two elongated vessels being gripped by the clamps, while maintaining the vessels in axial alignment with each other.

7. Apparatus for use in approximating the respective ends of two elongated vessels, said apparatus comprising:

clamping means for securely gripping the two vessels, without causing any substantial deformation thereof; and approximation means, to which said clamping means are coupled, for orienting the clamping means such that the two vessels gripped thereby are maintained in axial alignment with each other, and permitting the respective ends of the two vessels to be controllably moved from an initial position, where the respective ends are in spaced relationship, to a suturing position, where the respective ends are in proximity to each other, said approximation means including an elongated lead screw, first and second lead nuts threadedly engaging said lead screw, said clamping means being coupled to said respective lead nuts, and means for preventing rotation of said first and second lead nuts about the axis of said lead screw, whereby rotation of said lead screw causes said lead nuts to move toward each other and thereby approximate the respective ends of the two elongated vessels.

8. Apparatus for use in approximating the respective ends of two elongated vessels, to facilitate a suturing together of the vessels, said apparatus comprising:

first and second clamps for controllably gripping the respective vessels, each of said clamps including a first jaw having a gripping surface, a second jaw having a gripping surface disposed adjacent the gripping surface of said first jaw, and control means for controllably moving said first and second jaws toward each other, wherein the respective gripping surfaces of the jaws together form a seat for receiving the corresponding vessel and gripping it with a controllable pressure, without causing any significant deformation thereof; and support means for orienting said first and second clamps such that two vessels gripped thereby are maintained in spaced relationship and in axial alignment with respect to each other, said support means including an elongated lead screw having a first portion threaded in a first direction and a second portion threaded in a second direction, a first nut threadedly engaging the first portion of said lead screw, said first clamp being coupled to said first nut, a second nut threadedly engaging the second portion of said lead screw, said second clamp being coupled to said second nut, and means for inhibiting rotation of said first and second nuts about the axis of said lead screw, whereby rotation of said lead screw effects an axial movement of said first and second clamps toward each other, to approximate the respective ends of the two elongated vessels.

9. Apparatus for use in approximating the respective ends of two elongated vessels, to facilitate a suturing together of the vessels, said apparatus comprising:

first and second clamps for controllably gripping the respective vessels, each of said clamps including a first jaw having a gripping surface, a second jaw having a gripping surface disposed adjacent the gripping surface of said first jaw, and control means for controllably moving said first and second jaws toward each other, wherein the respective gripping surfaces of the jaws together form a seat for receiving the corresponding vessel and gripping it with a controllable pressure, without causing any significant deformation thereof; and support means for orienting said first and second clamps such that the two vessels gripped thereby are maintained in spaced relationship and in axial alignment with respect to each other, said support means including means for controllably moving said first and second clamp together, while maintaining the axial alignment, whereby an approximation of the elongated vessels is achieved;

wherein each of said first and second clamps further includes a stanchion having a base end coupled to said support means and a remote end for carrying said first jaw, and having a threaded portion on its exterior surface, and a pivot arm having a base end pivotally coupled to said stanchion, and a remote end for carrying said second jaw;

and wherein each of said control means includes a collar having an internally threaded portion for threadedly engaging the threaded portion of the corresponding stanchion, whereby rotation of the collar in a prescribed angular direction causes the collar to move toward the remote end of the stanchion and thereby urge the pivot arm to move in a pivotal fashion toward the stanchion.

10. Apparatus as defined in claim 9, wherein each of said stanchions includes an elongated slot for receiving the corresponding one of said pivot arms when the arm is urged toward the stanchion by said collar.

* * * * *